US008182839B2

(12) United States Patent
Engelhardt et al.

(10) Patent No.: US 8,182,839 B2
(45) Date of Patent: May 22, 2012

(54) PRODUCTION OF CELLULOSE NANOPARTICLES

(75) Inventors: Jurgen Engelhardt, Bad Fallingbostel (DE); Birgit Kosan, Rudolfstadt (DE); Christa Maria Kruger, Schneverdingen (DE); Frank Meister, Rudolfstadt (DE); Klaus Nachtkamp, Walsrode (DE); Jens Schaller, Apolda (DE)

(73) Assignee: Dow Global Technologies LLC, Midland, MI (US)

( * ) Notice: Subject to any disclaimer, the term of this patent is extended or adjusted under 35 U.S.C. 154(b) by 222 days.

(21) Appl. No.: 12/518,155

(22) PCT Filed: Nov. 29, 2007

(86) PCT No.: PCT/EP2007/010342
§ 371 (c)(1),
(2), (4) Date: Jan. 4, 2010

(87) PCT Pub. No.: WO2008/067942
PCT Pub. Date: Jun. 12, 2008

(65) Prior Publication Data
US 2010/0272819 A1     Oct. 28, 2010

(30) Foreign Application Priority Data
Dec. 8, 2006   (DE) .................. 10 2006 057 904

(51) Int. Cl.
*C08L 1/02*      (2006.01)
*C08J 3/12*      (2006.01)
*C08B 11/00*     (2006.01)
*C08B 37/00*     (2006.01)
*A61K 9/50*      (2006.01)

(52) U.S. Cl. ............... 424/495; 523/342; 106/167.01; 424/494; 424/489; 424/490; 536/56

(58) Field of Classification Search .................. None
See application file for complete search history.

(56) References Cited

U.S. PATENT DOCUMENTS

| | | | | |
|---|---|---|---|---|
| 4,278,790 | A | * | 7/1981 | McCormick .................. 536/84 |
| 6,541,627 | B1 | * | 4/2003 | Ono et al. ...................... 536/56 |
| 6,677,386 | B1 | * | 1/2004 | Giezen et al. .................. 516/31 |
| 6,858,725 | B1 | * | 2/2005 | Vladyka et al. ................ 536/56 |
| 7,687,477 | B2 | * | 3/2010 | Mikkonen et al. ............. 514/54 |
| 2003/0138490 | A1 | * | 7/2003 | Hu et al. ........................ 424/486 |
| 2003/0219490 | A1 | * | 11/2003 | Hovey et al. .................. 424/489 |
| 2005/0019412 | A1 | * | 1/2005 | Bosch et al. .................. 424/489 |

FOREIGN PATENT DOCUMENTS

| | | | |
|---|---|---|---|
| EP | 0 783 015 A1 | * | 7/1997 |
| EP | 0 850 979 A | * | 7/1998 |
| WO | WO 00/69916 A1 | * | 11/2000 |

OTHER PUBLICATIONS

Machine Translation of CN 1470552; pub'd Jan. 28, 2004; in China; Qing Qiang et al.; (retrieved online Jan. 12, 2012).*
Zimmerman et al.; Advanced Engineering Materials (2005), vol. 7, No. 12, pp. 1156-1161.*
Zimmerman et al.; Advanced Engineering Materials (2004), vol. 6, No. 9, pp. 754-761.*
Dufresne et al.; Polymer Composite (1997); vol. 18, No. 2, pp. 198-210.*

* cited by examiner

*Primary Examiner* — Robert A Wax
*Assistant Examiner* — Jeffrey T Palenik

(57) ABSTRACT

The present invention relates to novel nanoparticles based on cellulose and a process for producing them and their use.

12 Claims, 1 Drawing Sheet

PRODUCTION OF CELLULOSE NANOPARTICLES

CROSS REFERENCE TO RELATED APPLICATIONS

Figure 1:
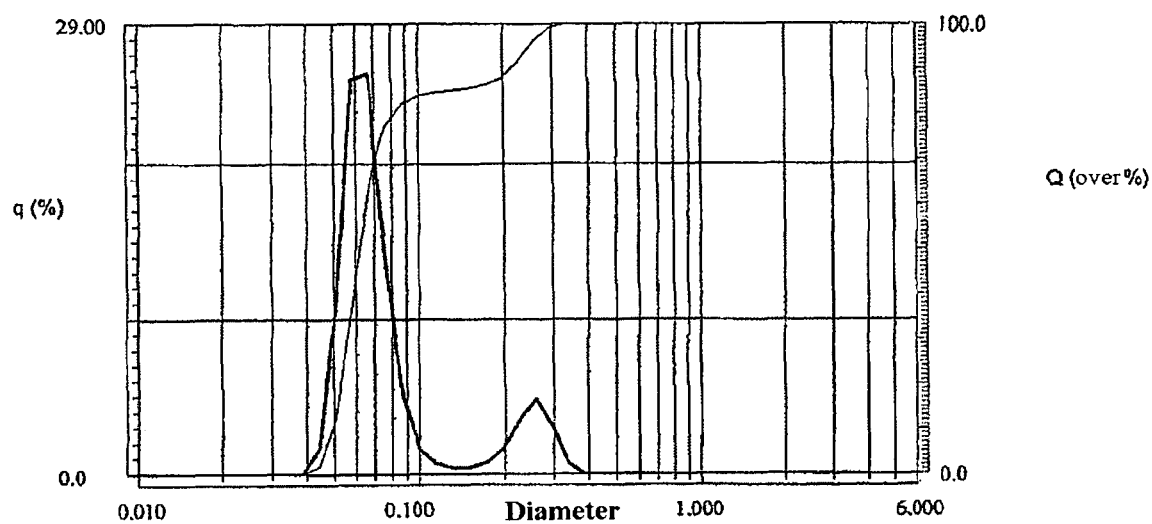

This application is a 35 USC §371 national phase filing of PCT/EP2007/010342 filed Nov. 29, 2007, which claims priority to DE 102006057904.6, filed Dec. 8, 2006.

The present invention relates to novel nanoparticles based on cellulose and a process for producing them and their use.

Nanotechnology is a technology of the future which will offer completely new opportunities to many fields. The altered ratio between surface area and mass in nanosize particles in particular results in completely new physicochemical properties such as color effects or lotus effect through to altered solubilities and drastically increased reactivity. Inorganic nanoparticles, e.g. particles based on $SiO_2$, $Al_2O_3$, $TiO_2$ or various modifications of carbon, are already commercially available.

The production of cellulosic nanoparticles has been described in various applications, but the methods employed there are restricted essentially to mechanical degradation or a combination of mechanical degradation methods and chemical degradation methods in which the cellulose is depolymerized by acid hydrolysis.

Thus, introduction of shear forces into an aqueous cellulose suspension and subsequent hydrolysis with sulfuric acid gave fibrils having a length of less than 200 nm. These fibrils displayed significant reinforcing effects in composites [T. Zimmermann, E. Pöhler, P. Schwaller: Mechanical and Morphological Properties of Cellulose Fibril Reinforced Nanocomposites, Advanced Engineering materials, 2005, Vol. 7, No. 12, pp. 1156-1161 and T. Zimmermann, E. Pöhler, T. Geiger: Cellulose Fibrils for Polymer Reinforcement, Advanced Engineering materials, 2004, Vol. 6, No. 9, pp. 754-761].

An even more complicated process is the production of cellulose whiskers from wheat straw [Alain Dufresne, Jean-Yves Cavaille, William Helbert: Polymer, Composite, 1997, Vol. 18, No. 2, 198-209]. Here, a wheat straw cellulose was firstly produced by steam explosion and the wheat straw particles having a size in the nanometer range (5 nm×150 to 300 nm) were subsequently obtained by sulfuric acid hydrolysis and concluding dialysis.

All these processes which are based on the chemical degradation of the cellulose polymer have serious disadvantages. As a result of degradation to glucose or water-soluble oligomers as undesirable by-products, losses in the mass of cellulose occur. The use of strong mineral acids makes complicated washing and purification steps necessary, complicates the process and is environmentally damaging. Industrial use of these methods on a relatively large scale is thus disadvantageous.

DE 60005932 T2 and EP 1159301 B1 describes the production of nanoparticles from biopolymers such as starch, in which hydrolytic degradation is dispensed with. However, these processes are of little importance from an industrial point of view since they require a series of mechanophysical treatments which are very complicated in engineering terms.

A simpler route is described in DE 10235729 A1, according to which particles having a size of less than 200 nm are obtained by controlled precipitation of substances from their solutions with the aid of surfactants or polyelectrolytes. In CN 1470552 A, this approach is applied to cellulose. Here, a "molecular dispersion" is subsequently produced and is subsequently subjected to "controlled sedimentation". The use of surfactants prevents agglomeration of the cellulose microfibrils to form larger structures. In this way, cellulose particles having an average particle size of from 50 to 200 nm were obtained and the abovementioned disadvantages of mechanochemical degradation of cellulose were able to be avoided. However, a disadvantage of this method is that the proportion of cellulose in the suspension before precipitation is only 0.1% by weight, which is prohibitive for efficient industrial production. Furthermore, the presence of surfactants is undesirable in many applications of cellulose derivatives, e.g. mortar and paints in the building industry and also cosmetic and pharmaceutical preparations, because of their surface-active properties. In the food, cosmetics and pharmaceutical sectors in particular, surfactants are virtually unusable because of their lack of biocompatibility.

It was therefore an object of the present invention to provide nanosize cellulose particles which can be obtained by a technically very simple process and do not have the abovementioned disadvantages of the prior art.

It has now surprisingly been found that such particles can be produced by adding cellulose ether as protective colloid instead of surfactants before precipitation of the cellulose particles.

The invention therefore provides a process for producing dispersions comprising cellulose nanoparticles having an average particle size of from 5 to 300 nm, determined by the method of dynamic laser light scattering, which comprises
   A) admixing a solution containing cellulose with
   B) a protective colloid comprising at least one ether based on polysaccharide and
   C) subsequently precipitating the cellulose by addition of a precipitant.

To produce the cellulose solution used in A), it is possible to use the types of cellulose which are known in principle to those skilled in the art. Examples are crystalline or microcrystalline cellulose, cotton cellulose, wood pulp cellulose, lignocellulose or cellulosic waste products. These typically have degrees of polymerization (DPs) of from 30 to 500, preferably from 60 to 150.

Such solutions are obtained by dissolving the base cellulose in a suitable solvent. Any insoluble residues which remain can be separated off by filtration or centrifugation and, if they contain cellulose, be reused for producing cellulose solutions.

Solvents used are the solvents which are known in principle to those skilled in the art for cellulose. These are preferably viscose, Cuoxam, Cuen, N-methylmorpholine N-oxide monohydrate, mixtures or solutions of N,N-dimethylacetamide/lithium chloride, dimethyl sulfoxide/paraformaldehyde or dimethyl sulfoxide/tetrabutylammonium fluoride, organic and inorganic acids and also systems based on sodium hydroxide, e.g. aqueous sodium hydroxide solution/thiourea, aqueous sodium hydroxide solution/urea or aqueous sodium hydroxide solution.

Particular preference is given to the systems based on sodium hydroxide of the abovementioned type; very particular preference is given to aqueous sodium hydroxide solution.

If aqueous sodium hydroxide solution is employed for producing the cellulose solutions, it preferably has an NaOH concentration of from 2 to 25% by weight, particularly preferably from 5 to 12% by weight.

The preferably basic cellulose solutions which can be obtained in this way and are used in A) preferably have a concentration of cellulose homogeneously dissolved therein of from 0.1 to 20% by weight, particularly preferably from 3 to 8% by weight.

As protective colloids added in B), it is possible to use the ethers based on polysaccharides such as starch or cellulose which are known in principle to those skilled in the art. Preferred protective colloids are cellulose ethers. Preferred cellulose ethers are nonionic cellulose ethers, among which low-viscosity hydroxyalkylcelluloses and methylhydroxyalkylcelluloses are preferred.

The protective colloids can be either partially or completely soluble or swellable in water.

The protective colloids are preferably used as aqueous, if appropriate alkyl-containing solutions in B).

These have concentrations based on the cellulose ethers present therein of from 0.1 to 10% by weight, particularly preferably from 1 to 3% by weight.

The amount of protective colloid used in B) based on the cellulose used in solution form in A) is preferably from 20 to 120% by weight, particularly preferably from 45 to 60% by weight.

Preference is given to using exclusively cellulose ethers as protective colloids in B).

As precipitant in C), it is possible to use all nonsolvents for cellulose which are known to those skilled in the art. These are preferably aqueous systems, alcohols, ketones and mixtures thereof. Particular preference is given to mixtures of dilute aqueous acids and $C_1$-$C_4$-alcohols or $C_3$-$C_{10}$-ketones. Very particular preference is given to mixtures of dilute acids and isopropanol or acetone.

As dilute acids, it is possible to use sulfuric acid or hydrochloric acid, with the amount of acid preferably being selected so that it just neutralizes the aqueous sodium hydroxide solution used for producing the cellulose solution.

If mixtures of water and alcohols or ketones are used for the precipitation, they preferably have a ratio of water to alcohol or ketone of from 2 to 10% by weight, particularly preferably from 6 to 8% by weight.

The precipitation solution C) is preferably used in amounts of from 10 to 100% by weight, particularly preferably from 30 to 50% by weight, based on the cellulose used in solution form in A).

The process of the invention is carried out at temperatures of preferably from 5 to 50° C., particularly preferably from 15 to 25° C.

In a preferred embodiment, the cellulose solution to which the protective colloid has been added is subjected to high shear before, during and/or after addition of the precipitation solution C), which promotes the formation of very small particles. The described methods which are known to those skilled in the art, e.g. microfluidizers or high-speed stirrers operating according to the rotor-stator principle, are preferably used for this purpose.

High-speed stirrers operating according to the rotor-stator principle are, for example, Ultra-Turrax apparatuses as are used as dispersing apparatuses for emulsifying, homogenizing and suspending flowable media. The effective frequency can be set and can be matched to the material or mixture to be processed. The shearing times employed here are usually from 1 to 30 minutes at a speed of rotation of from 6000 to 18 000 rpm, preferably from 2 to 10 minutes at from 10 000 to 14 000 rpm.

The principle of a microfluidizer can be described as follows. The material to be processed is passed under high pressure through an interaction chamber. The sample flows through one or two narrow channels and reaches linear velocities of up to 1000 m/s, depending on the type of apparatus. This results in tremendous shear forces. There are no moving parts in the chamber, which ensures a narrow particle and droplet size distribution.

The introduction of energy during shearing can in principle be effected in one or more stages and also continuously with variable energy input.

The cellulose nanoparticles according to the invention which can be obtained in this way preferably have an average particle size determined by means of dynamic laser light scattering of from 40 nm to 300 nm, preferably from 40 nm to 200 nm, particularly preferably from 60 nm to 100 nm.

Preference is given to at least 50% by weight, particularly preferably at least 80% by weight, very particularly preferably at least 95% by weight, of the particles according to the invention having the abovementioned sizes.

The invention further provides cellulose nanoparticles having a cellulose-based core and a surrounding shell based on cellulose ethers, wherein these particles have an average particle size determined by means of dynamic laser light scattering in accordance with BS ISO 13323-1 of from 5 to 300 nm.

The shell surrounding the cellulose-based core is formed essentially by the cellulose ethers added as protective colloid in step B) of the production process, as have been described above.

The proportion by weight in the dry state of the enveloping colloid relative to the cellulose core is preferably from 200 to 5% by weight, particularly preferably from 50 to 20% by weight.

The cellulose present in nanoparticulate form typically has degrees of polymerization DP of from 30 to 500, particularly preferably from 60 to 150.

The present invention further provides dispersions containing the cellulose nanoparticles of the invention.

These dispersions typically have concentrations based on the cellulose particles dispersed therein of from 0.05 to 10% by weight, particularly preferably from 1 to 3% by weight.

These dispersions have pH values of from 3 to 12, particularly preferably from 6 to 8.

These dispersions have residual salt contents of from 3 to 15% by weight, particularly preferably from 7 to 11% by weight.

The particles according to the invention and their dispersions are suitable as functional additives and ingredients, for example in pharmaceutical or cosmetic preparations, food preparations and also in building materials, varnishes, paints, coating compounds and polymers.

EXAMPLES

The particles sizes were determined using a dynamic laser light scattering apparatus, Horiba LB 550, in accordance with BS ISO 13323-1. For this purpose, 1 ml of a 1-1.5% strength by weight sample was introduced into a glass or acrylic disposable sill and measured for 1 minute.

Example 1

A matured wood pulp having a Cuoxam DP of 134 was added in a ratio of 1/22 to 10% strength by weight aqueous sodium hydroxide solution which had been cooled to 10° C. and the mixture was stirred for 30 minutes while cooling. After centrifuging off the supernatant solution from the insoluble residue, a cellulose solution in aqueous sodium hydroxide having a proportion by mass of cellulose of about 3% by weight based on the total solution was obtained. The insoluble residue can be reused.

TABLE 1

Data for example 1

| Cellulose | Weight used (g) | Mass, dissolved (g) | Mass of residue (g) | Conc. of the cellulose in the solution | Cuoxam DP, dissolved cellulose | Cuoxam DP, residue |
|---|---|---|---|---|---|---|
| Matured wood pulp | 35.0 | 22.2 | 14.6 | 29.% by wt. | 75 | 139 |

0.5 part of a 3.5% strength by weight aqueous hydroxyethylcellulose solution was added to this cellulose solution, based on the solution volume. This mixture of cellulose solution and protective colloid was stirred by means of an Ultraturrax [IKA T25 basic, 25 mm stirrer diameter] at 6000 rpm. To prepare the precipitation solution, a 10% strength by weight sulfuric acid was mixed with isopropanol in a ratio of 6/1. The amount of precipitation solution to be used was calculated so that addition to the basic cellulose solution resulted in a neutral suspension. The addition of the previously prepared precipitant was carried out while stirring at 6000 rpm. The mixture was stirred further for another 3 minutes.

Over 80% of the cellulose nanoparticles present in the suspension was smaller than 100 nm (FIG. 1 shows particle size distribution of the cellulose nanosuspensions produced as described in example 1, measured by means of laser light scattering).

The cellulose nanosuspension was used for a comparative viscosity measurement. The comparative suspension consisted of the same components but the protective colloid was added only after precipitation was complete, so that it could no longer display its stabilizing action. The cellulose nanosuspension produced as described in example 1 had a slightly increased viscosity compared to the comparative suspension described. It can be concluded from this that the nanoparticles interact with the surrounding water to an increased extent because of their greatly increased surface area.

Example 2

Using a method analogous to example 1, a cellulose nanosuspension in which over 80% of the cellulose nanoparticles was smaller than 300 nm was obtained from a wood pulp having a Cuoxam DP of 389.

TABLE 2

Data for example 2

| Cellulose | Weight used (g) | Mass, dissolved (g) | Mass of residue (g) | Conc. of the cellulose in the solution | Cuoxam DP, dissolved cellulose | Cuoxam DP, residue |
|---|---|---|---|---|---|---|
| Wood pulp | 12.5 | 2.2 | 10.0 | 0.8% by wt. | 139 | 406 |

Comparison of the viscosities of the cellulose suspension produced and a comparative solution indicated a slightly increased viscosity of the cellulose suspension compared to the comparative solution.

Example 3

Commercial wood pulp having a Cuoxam DP of 521 was shaken in Cuoxam solution for 5 hours so as to give a 1% strength by weight cellulose solution.

0.5 part of a 3.5% strength by weight hydroxypropylcellulose solution was added to this cellulose solution based on the solution volume. This mixture of cellulose solution and protective colloid was stirred by means of an Ultraturrax [IKA T25 basic, 25 mm stirrer diameter] at 6000 rpm. While stirring, 10% strength by weight sulfuric acid was added in such an amount that a neutral suspension resulted. The addition was likewise carried out while stirring at 6000 rpm. The mixture was stirred further for another 3 minutes.

Over 80% of the cellulose nanoparticles present in the suspension is smaller than 300 nm.

Comparison of the viscosities of the cellulose suspension produced and a comparative solution indicated a slightly increased viscosity of the cellulose suspension compared to the comparative solution.

Example 4

Microcrystalline cellulose having a Cuoxam DP of 181 was added in a ratio of 1/22 to 6% strength by weight aqueous sodium hydroxide solution containing 4% by weight of urea.

After storing the mixture at −20° C. for 5 hours and allowing it to stand at room temperature, a cellulose solution having a cellulose content of 3% by weight was obtained. The small amount of insoluble material was centrifuged off and can be reused.

0.33 part of a 3.5% strength by weight methylhydroxypropylcellulose solution was added to this cellulose solution, based on the solution volume. This mixture of cellulose solution and protective colloid was stirred by means of an Ultraturrax [IKA T25 basic, 25 mm stirrer diameter] at 8000 rpm. While stirring, 10% strength by weight sulfuric acid was added in such an amount that a neutral suspension resulted. The addition was carried out while stirring at 8000 rpm. The mixture was stirred further for another 3 minutes.

85% of the cellulose nanoparticles present in the suspension was smaller than 150 nm.

Comparison of the viscosities of the cellulose suspension produced and a comparative solution indicated a slightly increased viscosity of the cellulose suspension compared to the comparative solution.

The invention claimed is:

1. A process for producing dispersions comprising cellulose nanoparticles having an average particle size of from 5 to 300 nm, determined by the method of dynamic laser light scattering in accordance with BS ISO 13323-1, which comprises
   A) admixing a solution comprising cellulose with
   B) a protective colloid comprising at least one ether based on polysaccharide and
   C) subsequently precipitating the cellulose by addition of a precipitant.

2. The process as claimed in claim 1, wherein the cellulose solutions used in A) are obtained by dissolving cellulose in one or more solvents from the group consisting of viscose, Cuoxam, Cuen, N-methylmorpholine N-oxide monohydrate, N,N-dimethylacetamide/lithium chloride, dimethyl sulfoxide/paraformaldehyde, dimethyl sulfoxide/tetrabutylammonium fluoride, aqueous sodium hydroxide solution/thiourea and aqueous sodium hydroxide solution/urea mixtures and organic or inorganic acids and aqueous sodium hydroxide solution.

3. The process as claimed in claim 1 wherein the cellulose solutions used in A) have a cellulose concentration of from 0.1 to 20% by weight.

4. The process as claimed in claim 1 wherein the protective colloids used in B) are cellulose ethers.

5. The process as claimed in claim 1 wherein the amount of protective colloid used in B) based on the cellulose used in solution form in A) is from 20 to 120% by weight.

6. The process as claimed in claim 1 wherein water-containing systems, alcohols, ketones and mixtures thereof are used as precipitant in C).

7. The process as claimed in claim 1 wherein at least 80% of the cellulose particles obtained after precipitation have a size of from 60 nm to 100 nm determined by means of dynamic laser light scattering in accordance with BS ISO 13323-1.

8. The process as claimed in claim 2 wherein the cellulose solutions used in A) have a cellulose concentration of from 0.1 to 20% by weight.

9. The process as claimed in claim 8 wherein the protective colloids used in B) are cellulose ethers.

10. The process as claimed in claim 9 wherein the amount of protective colloid used in B) based on the cellulose used in solution form in A) is from 20 to 120% by weight.

11. The process as claimed in claim 10 wherein water-containing systems, alcohols, ketones and mixtures thereof are used as precipitant in C).

12. The process as claimed in claim 11 wherein at least 80% of the cellulose particles obtained after precipitation have a size of from 60 nm to 100 nm determined by means of dynamic laser light scattering in accordance with BS ISO 13323-1.

* * * * *